US007888562B2

(12) United States Patent
Liu et al.

(10) Patent No.: US 7,888,562 B2
(45) Date of Patent: Feb. 15, 2011

(54) PLASTID TRANSFORMATION SYSTEM TO PREVENT THE INTRAMOLECULAR RECOMBINATION OF TRANSGENE

(75) Inventors: Jang Ryol Liu, Taejeon-si (KR); Hwa-Jee Chung, Taejeon-si (KR); Sung Ran Min, Taejeon-si (KR); Won Joong Jeong, Taejeon-si (KR); Ju Young Park, Taejeon-si (KR)

(73) Assignee: Korea Research Institute of Bioscience and Biotechnology (KR)

( * ) Notice: Subject to any disclaimer, the term of this patent is extended or adjusted under 35 U.S.C. 154(b) by 231 days.

(21) Appl. No.: 12/159,595

(22) PCT Filed: Oct. 25, 2006

(86) PCT No.: PCT/KR2006/004377

§ 371 (c)(1),
(2), (4) Date: Jun. 27, 2008

(87) PCT Pub. No.: WO2007/091756

PCT Pub. Date: Aug. 16, 2007

(65) Prior Publication Data

US 2008/0301834 A1     Dec. 4, 2008

(30) Foreign Application Priority Data

Feb. 9, 2006     (KR)     ...................... 10-2006-0012477

(51) Int. Cl.
*C12N 15/82* (2006.01)
*A01H 5/00* (2006.01)
(52) U.S. Cl. ..................... 800/298; 800/278; 435/320.1
(58) Field of Classification Search ........................ None
See application file for complete search history.

(56) References Cited

U.S. PATENT DOCUMENTS 6,376,744 B1 *   4/2002   Maliga et al.   ................ 800/278
6,624,296 B1 *   9/2003   Maliga et al.   .............. 536/24.1

FOREIGN PATENT DOCUMENTS

WO     WO 99/10513     *   3/1999

OTHER PUBLICATIONS

Herz et al., "Development of novel types of plastid transformation vectors and evaluation of factors controlling expression," *Transgenic Research*, 14(6):969-982, (2005).
Kavanagh et al., "Homologous Plastid DNA Transformation in Tobacco Is Mediated by Multiple Recombination Events," *Genetics*, 152:1111-1122 (1999).
Staub et al., "Extrachromosomal elements in tobacco plastids," *Proceedings of National Academy of Science*, 91:7468-7472 (1994).

* cited by examiner

*Primary Examiner*—Anne Kubelik
(74) *Attorney, Agent, or Firm*—Klarquist Sparkman, LLP

(57) ABSTRACT

The present invention relates to a plastid transformation system capable of preventing second recombination events of heterologous genes inserted into plastid genomes. More specifically, this invention relates to a plastid transformation vector carrying a promoter and a terminator derived from organisms other than tobacco. The inventive recombinant expression vector for plastid transformation is capable of mass-producing exogenous proteins on a level par with conventional vectors carrying promoter/terminator couples of tobacco origin. At the same time, it is capable of preventing second recombination events within plastids. Thus, the vector of this invention is greatly useful in producing transgenic plants since it can effect a secure introduction of heterologous genes and support normal transformation and heterologous gene expression.

11 Claims, 10 Drawing Sheets

[Fig. 1]
a
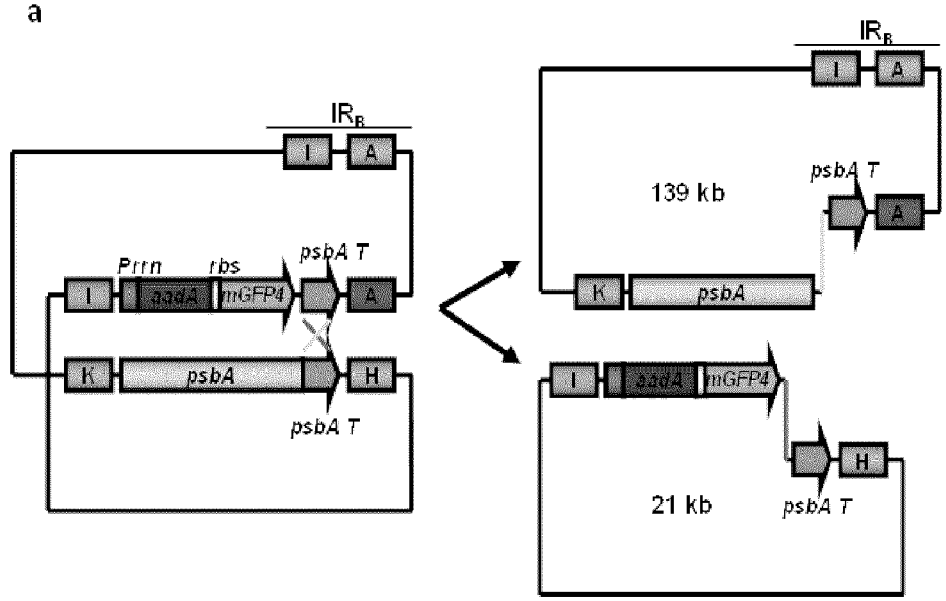
b
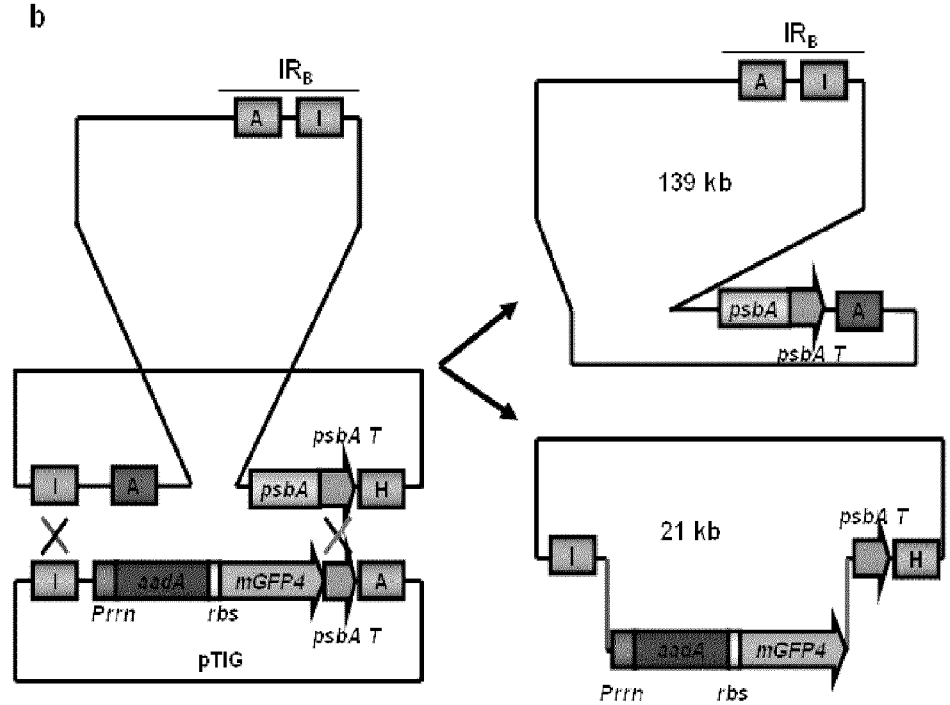

[Fig. 2]
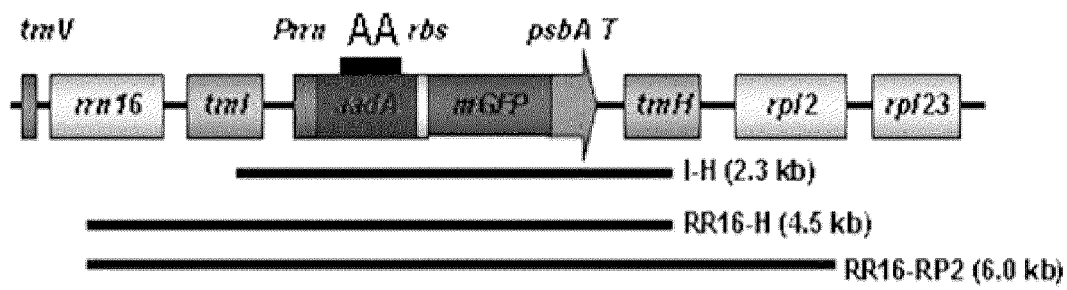
[Fig. 3]
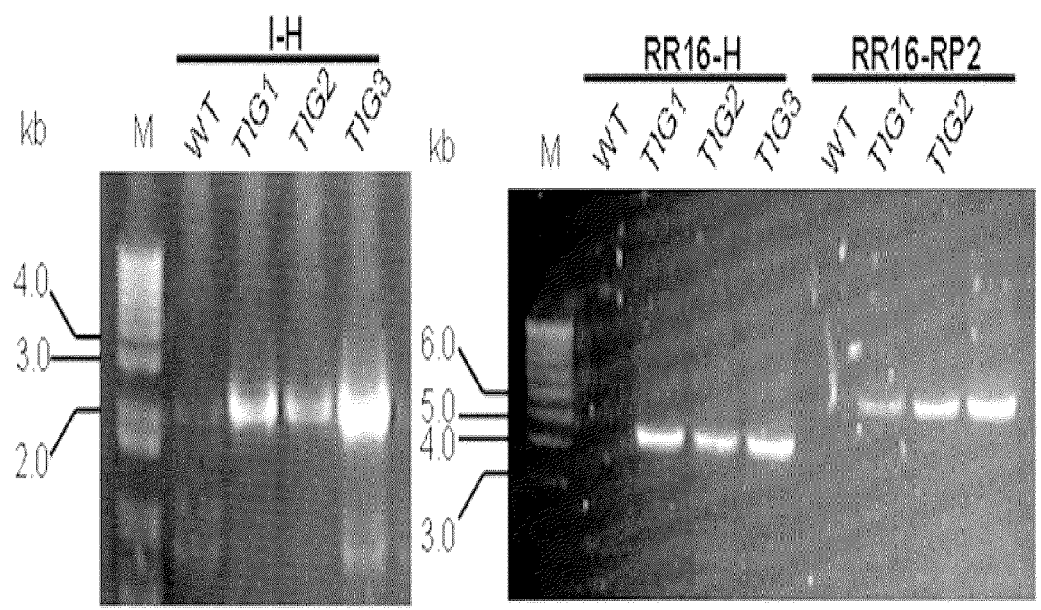

[Fig. 4]
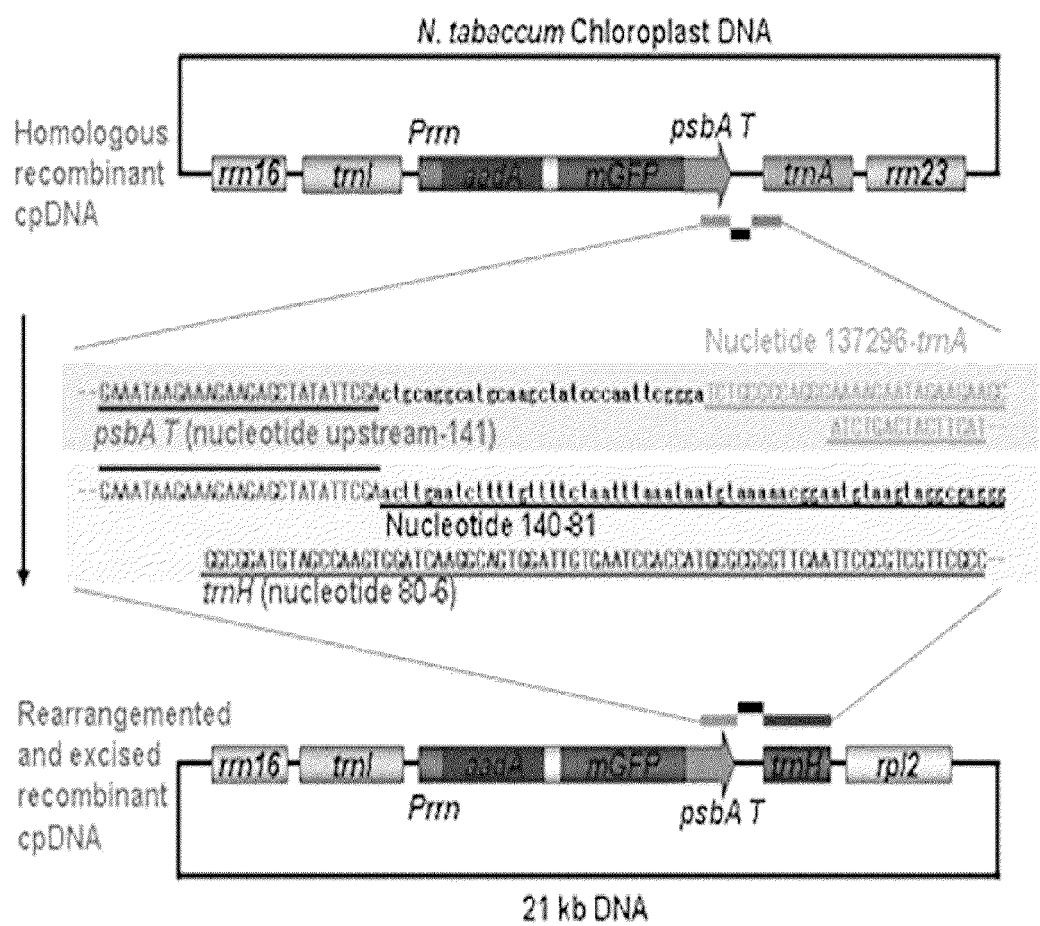
[Fig. 5]
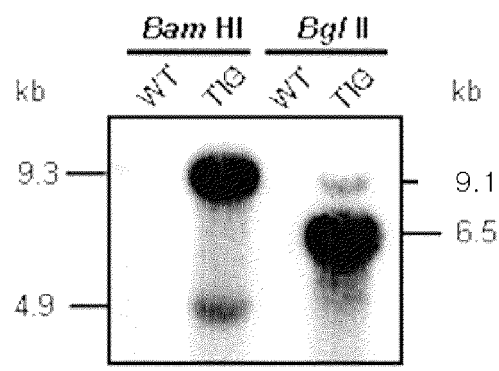

[Fig. 6]
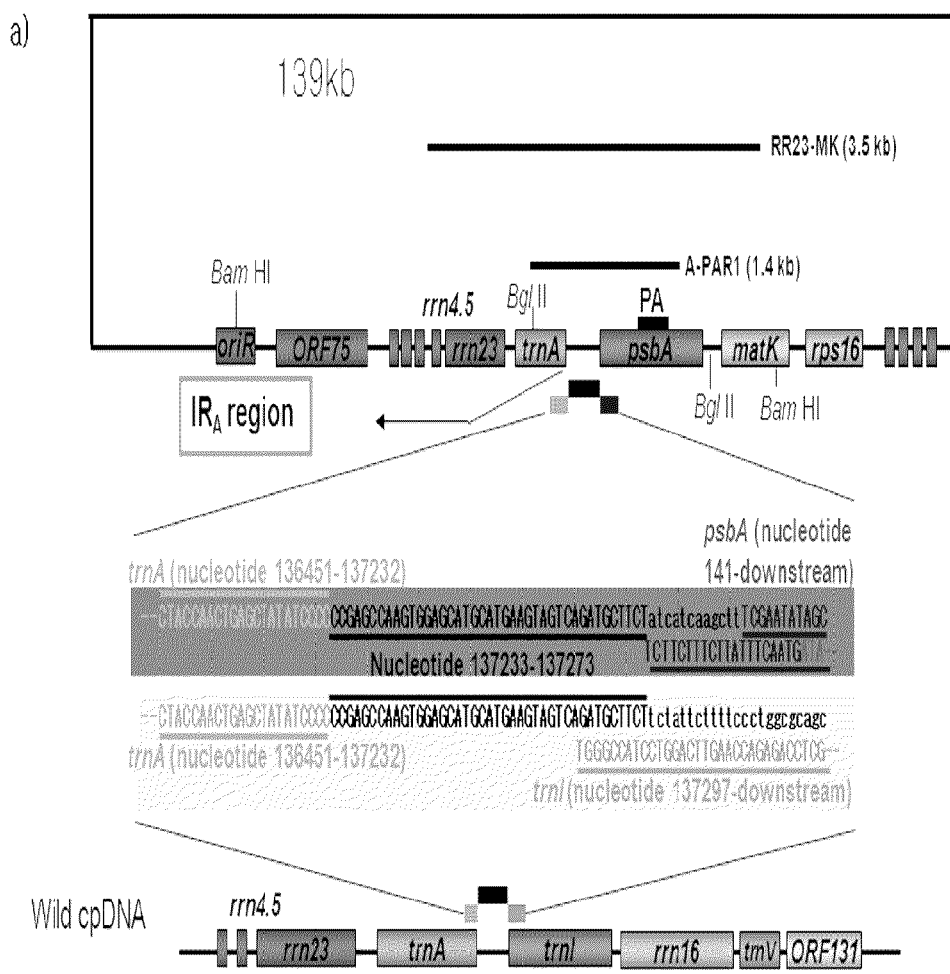
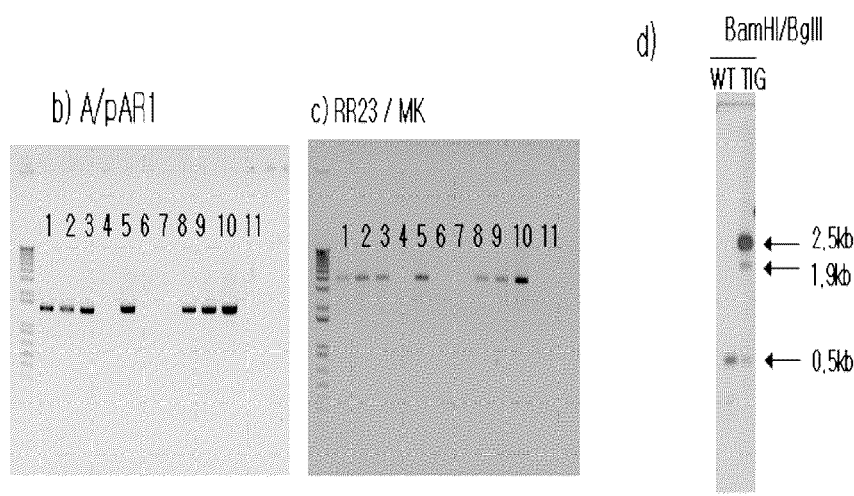

[Fig. 7]
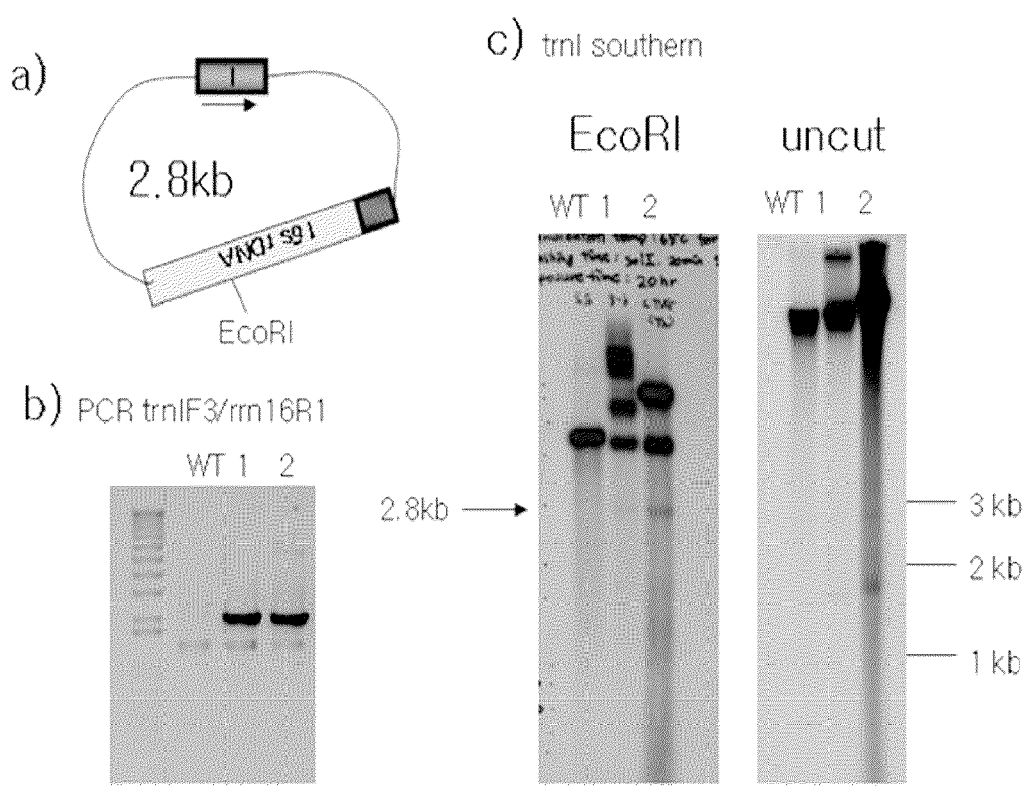

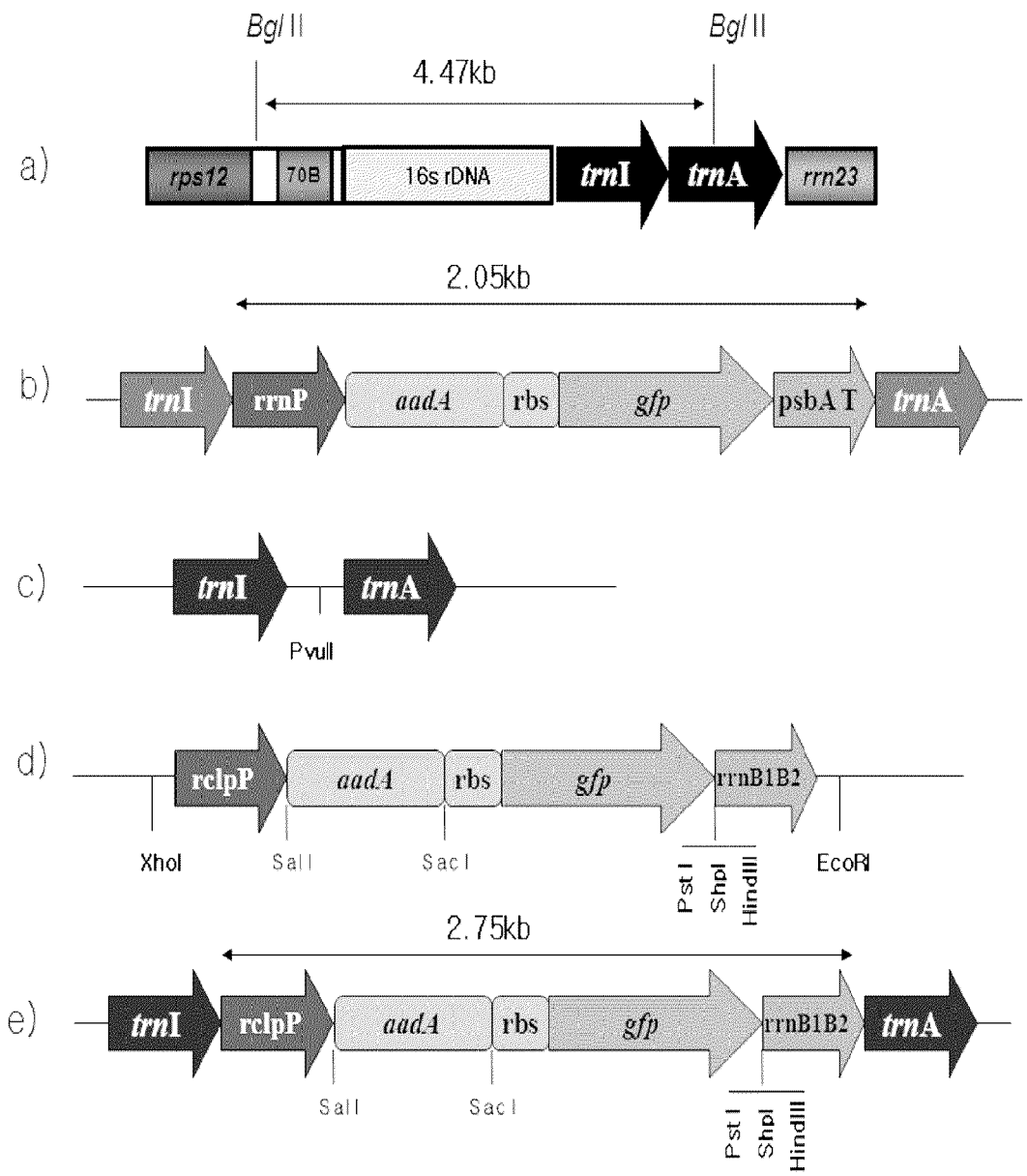
[Fig. 8]

[Fig. 9]
a) aadA probe
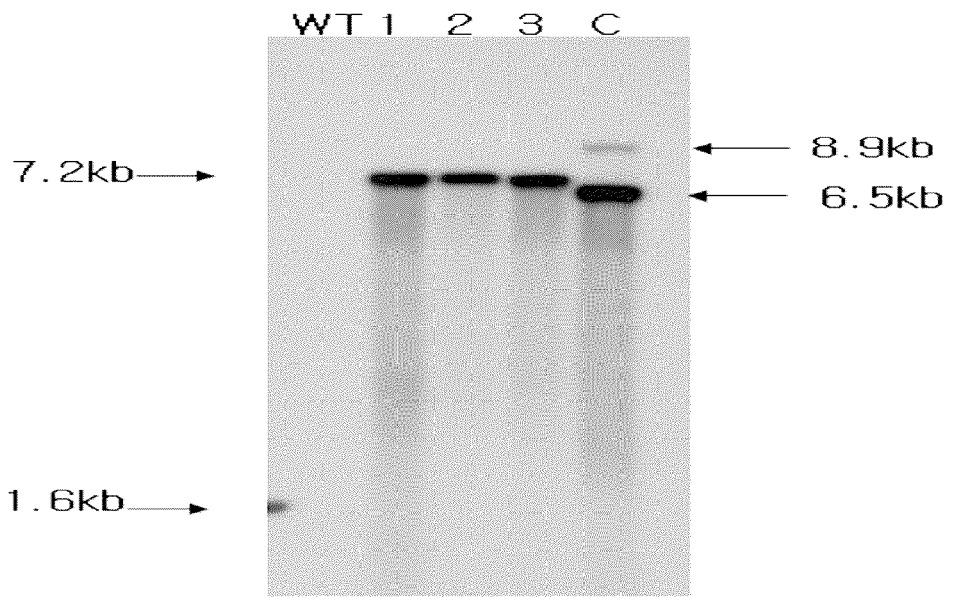
b) trnA probe
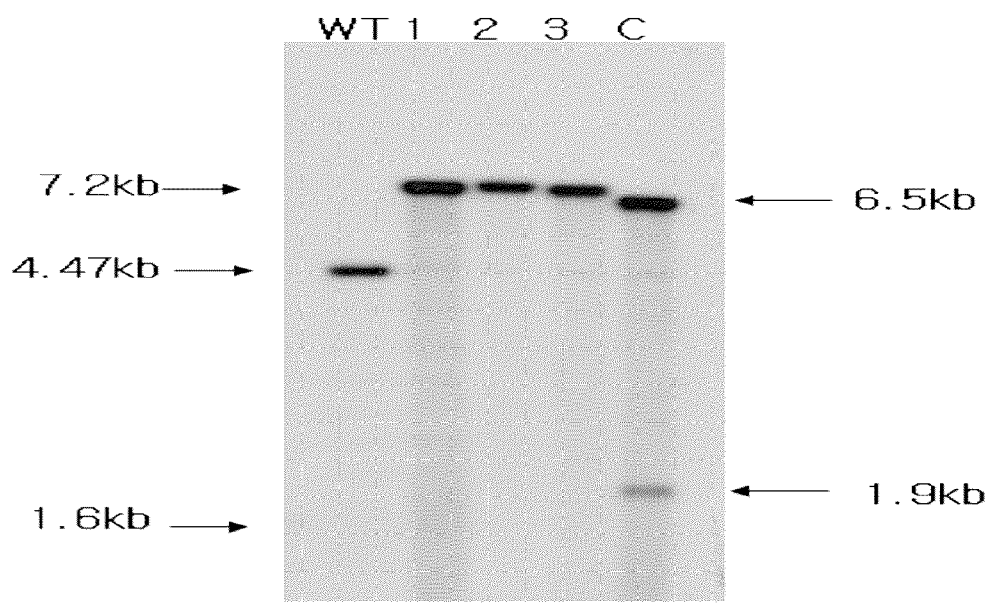

[Fig. 10]
a) I/A
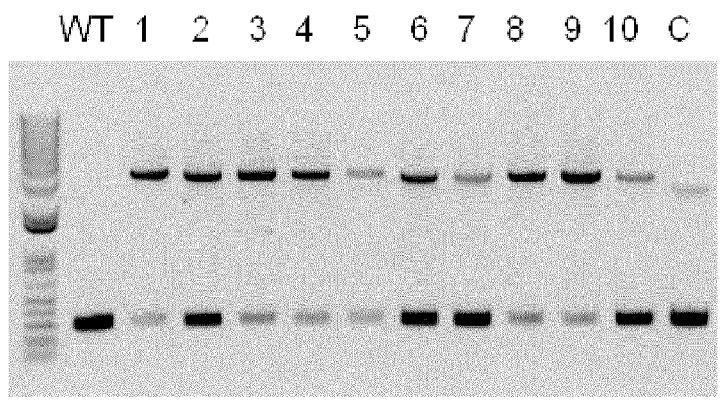
b) VH
21kb
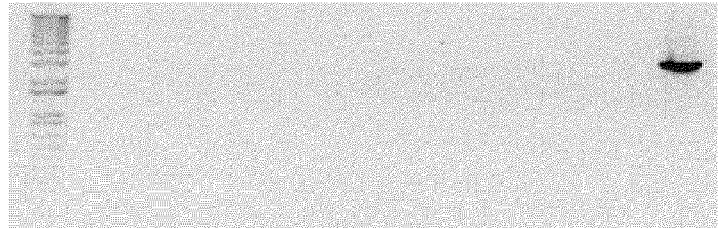
c) RR23/MK
139kb
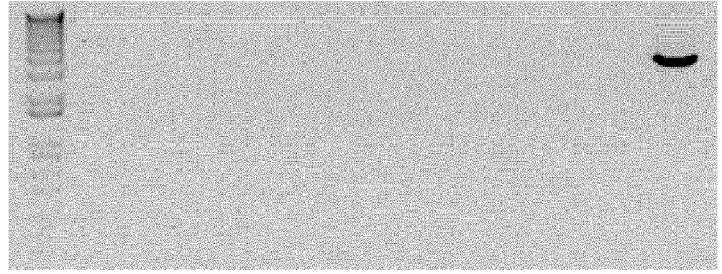

[Fig. 11]
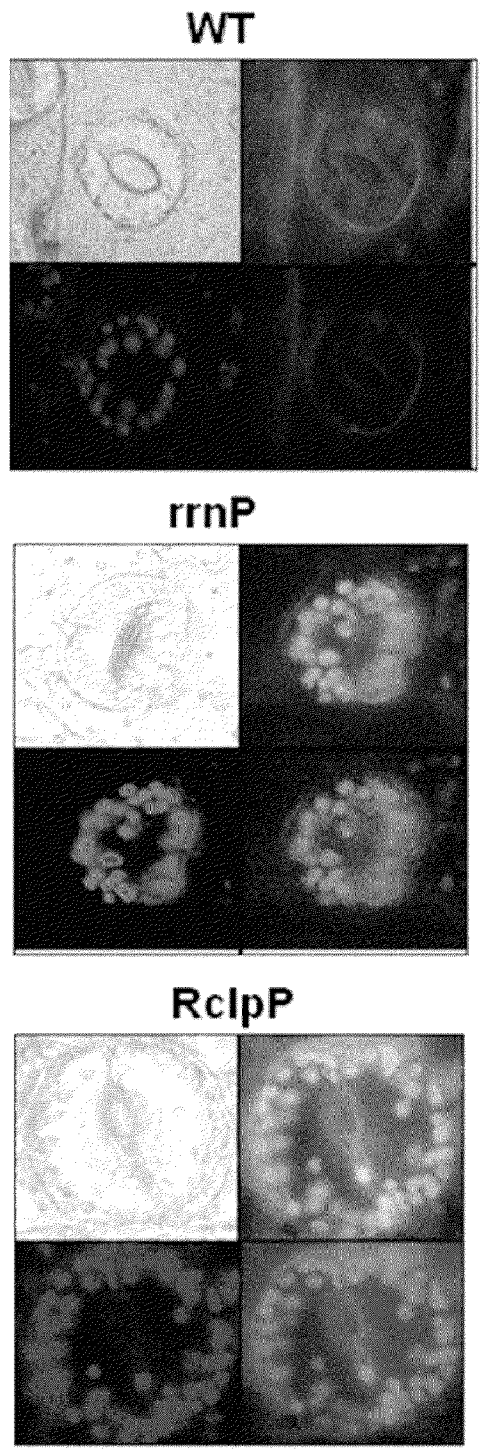

[Fig. 12]
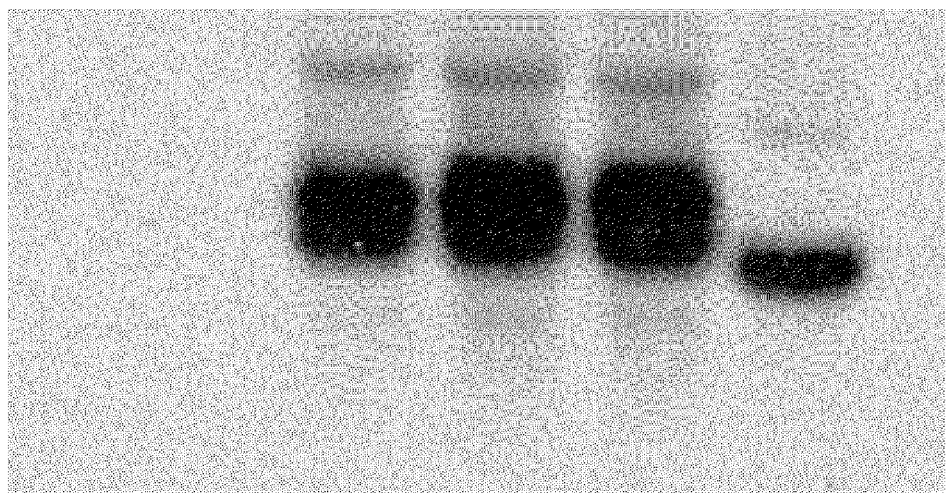
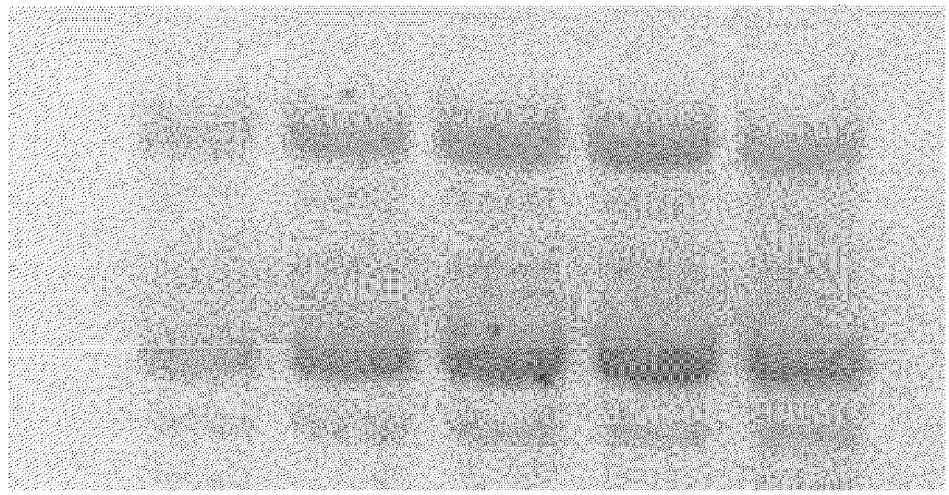

```
                        SEQUENCE LISTING

<160> NUMBER OF SEQ ID NOS: 28

<210> SEQ ID NO 1
<211> LENGTH: 261
<212> TYPE: DNA
<213> ORGANISM: Artificial Sequence
<220> FEATURE:
<223> OTHER INFORMATION: clp promoter

<400> SEQUENCE: 1
gcttatttgg aaaaaacgaa gaatagatcc ctatctcttt ttgtttagta ttcgaatcac     60
cattcttttt tctttattca atctgtctta tcctacttat atgtataatc tttcaatcta    120
tgtattattt caatctacgt acttaataga atctatagta ttcatataga ataagaaaaa    180
aacgtgaaaa caataaactg cggattcttt ctttctcttc cattcttacg tttccatatt    240
aaagtgtagt tttcttactt a                                              261

<210> SEQ ID NO 2
<211> LENGTH: 781
<212> TYPE: DNA
<213> ORGANISM: Artificial Sequence
<220> FEATURE:
<223> OTHER INFORMATION: rrnB1/B2 terminator

<400> SEQUENCE: 2
ctgcaggcat gcaagcttgg ctgttttggc ggatgagaga agattttcag cctgatacag     60
```

-continued

```
attaaatcag aacgcagaag cggtctgata aaacagaatt tgcctggcgg cagtagcgcg    120
gtggtcccac ctgaccccat gccgaactca gaagtgaaac gccgtagcgc cgatggtagt    180
gtggggtctc cccatgcgag agtagggaac tgccaggcat caaataaaac gaaaggctca    240
gtcgaaagac tgggcctttc gttttatctg ttgtttgtcg gtgaacgctc tcctgagtag    300
gacaaatccg ccgggagcgg atttgaacgt tgcgaagcaa cggcccggag ggtggcgggc    360
aggacgcccg ccataaactg ccaggcatca aattaagcag aaggccatcc tgacggatgg    420 ccttttttgcg tttctacaaa ctcttttgtt tattttttcta aatacattca aatatgtatc    480
cgctcatgag acaataaccc tgataaatgc ttcaataata ttgaaaaagg aagagtatga    540
gtattcaaca tttccgtgtc gcccttattc cctttttttgc ggcattttgc cttcctgttt    600
ttgctcaccc agaaacgctg gtgaaagtaa aagatgctga agatcagttg ggtgcacgag    660
tgggttacat cgaactggat ctcaacagcg gtaagatcct tgagagtttt cgccccgaag    720
aacgttttcc aatgatgagc acttttaaag ttctgctatg tggcgcggta ttatcccgtg    780
t                                                                     781

<210> SEQ ID NO 3
<211> LENGTH: 26
<212> TYPE: DNA
<213> ORGANISM: Artificial Sequence
<220> FEATURE:
<223> OTHER INFORMATION: rclpP5 primer

<400> SEQUENCE: 3
gcgctgcagc ttatttggaa aaaacg                                           26

<210> SEQ ID NO 4
<211> LENGTH: 33
<212> TYPE: DNA
<213> ORGANISM: Artificial Sequence
<220> FEATURE:
<223> OTHER INFORMATION: rclpP3 primer

<400> SEQUENCE: 4
gcgtcgactc cctcctaagt aagaaaacta cac                                   33

<210> SEQ ID NO 5
<211> LENGTH: 23
<212> TYPE: DNA
<213> ORGANISM: Artificial Sequence
<220> FEATURE:
<223> OTHER INFORMATION: I primer

<400> SEQUENCE: 5
ccgtaggtgc gatgatttac ttc                                              23

<210> SEQ ID NO 6
<211> LENGTH: 20
<212> TYPE: DNA
<213> ORGANISM: Artificial Sequence
<220> FEATURE:
<223> OTHER INFORMATION: H primer

<400> SEQUENCE: 6
acgggaattg aacccgcgca                                                  20

<210> SEQ ID NO 7
<211> LENGTH: 17
<212> TYPE: DNA
<213> ORGANISM: Artificial Sequence
```

-continued

```
<220> FEATURE:
<223> OTHER INFORMATION: RP2 primer

<400> SEQUENCE: 7
cccgagcaca cgcaatg                                                      17

<210> SEQ ID NO 8
<211> LENGTH: 20
<212> TYPE: DNA
<213> ORGANISM: Artificial Sequence
<220> FEATURE:
<223> OTHER INFORMATION: RP16 primer

<400> SEQUENCE: 8
cagcagccgc ggtaatacag                                                   20

<210> SEQ ID NO 9
<211> LENGTH: 23
<212> TYPE: DNA
<213> ORGANISM: Artificial Sequence
<220> FEATURE:
<223> OTHER INFORMATION: A primer

<400> SEQUENCE: 9
agagtctttc agtggcacgt ttc                                               23

<210> SEQ ID NO 10
<211> LENGTH: 20
<212> TYPE: DNA
<213> ORGANISM: Artificial Sequence
<220> FEATURE:
<223> OTHER INFORMATION: PAF1 primer

<400> SEQUENCE: 10
aaaggagcaa tagcaccctc                                                   20

<210> SEQ ID NO 11
<211> LENGTH: 21
<212> TYPE: DNA
<213> ORGANISM: Artificial Sequence
<220> FEATURE:
<223> OTHER INFORMATION: pAR1 primer

<400> SEQUENCE: 11
acaacggtgg tccttatgaa c                                                 21

<210> SEQ ID NO 12
<211> LENGTH: 20
<212> TYPE: DNA
<213> ORGANISM: Artificial Sequence
<220> FEATURE:
<223> OTHER INFORMATION: RR23 primer

<400> SEQUENCE: 12
cctgcccatg gattcagcag                                                   20

<210> SEQ ID NO 13
<211> LENGTH: 20
<212> TYPE: DNA
<213> ORGANISM: Artificial Sequence
<220> FEATURE:
<223> OTHER INFORMATION: MK primer

<400> SEQUENCE: 13
gaccgatttg ggcgtatatg                                                   20
```

```
<210> SEQ ID NO 14
<211> LENGTH: 20
<212> TYPE: DNA
<213> ORGANISM: Artificial Sequence
<220> FEATURE:
<223> OTHER INFORMATION: trnIF3 primer

<400> SEQUENCE: 14
ctcgagcaca ggtttagcaa                                              20

<210> SEQ ID NO 15
<211> LENGTH: 19
<212> TYPE: DNA
<213> ORGANISM: Artificial Sequence
<220> FEATURE:
<223> OTHER INFORMATION: rrn16R1 primer

<400> SEQUENCE: 15
gaacgaattc accgccgta                                               19

<210> SEQ ID NO 16
<211> LENGTH: 19
<212> TYPE: DNA
<213> ORGANISM: Artificial Sequence
<220> FEATURE:
<223> OTHER INFORMATION: aad5 primer

<400> SEQUENCE: 16
ccctggagag agcgagatt                                               19

<210> SEQ ID NO 17
<211> LENGTH: 19
<212> TYPE: DNA
<213> ORGANISM: Artificial Sequence
<220> FEATURE:
<223> OTHER INFORMATION: aad3 primer

<400> SEQUENCE: 17
ttcaagtatg acgggctga                                               19

<210> SEQ ID NO 18
<211> LENGTH: 20
<212> TYPE: DNA
<213> ORGANISM: Artificial Sequence
<220> FEATURE:
<223> OTHER INFORMATION: trnIR4 priemr

<400> SEQUENCE: 18
cacctacggt ccaaccaatt                                              20

<210> SEQ ID NO 19
<211> LENGTH: 20
<212> TYPE: DNA
<213> ORGANISM: Artificial Sequence
<220> FEATURE:
<223> OTHER INFORMATION: trnAF1 primer

<400> SEQUENCE: 19
tgcgattacg ggttggatgt                                              20

<210> SEQ ID NO 20
<211> LENGTH: 20
<212> TYPE: DNA
<213> ORGANISM: Artificial Sequence
<220> FEATURE:
<223> OTHER INFORMATION: trnAR1 primer
```

<400> SEQUENCE: 20
gttcttgaca gcccatcttt                                            20

<210> SEQ ID NO 21
<211> LENGTH: 25
<212> TYPE: DNA
<213> ORGANISM: Artificial Sequence
<220> FEATURE:
<223> OTHER INFORMATION: I-L1 primer

<400> SEQUENCE: 21
gctctagatt ctcgacggtg aagta                                      25

<210> SEQ ID NO 22
<211> LENGTH: 25
<212> TYPE: DNA
<213> ORGANISM: Artificial Sequence
<220> FEATURE:
<223> OTHER INFORMATION: I-R2 primer

<400> SEQUENCE: 22
ggggtacctt aaggctatgc catcc                                      25

<210> SEQ ID NO 23
<211> LENGTH: 24
<212> TYPE: DNA
<213> ORGANISM: Artificial Sequence
<220> FEATURE:
<223> OTHER INFORMATION: GFP(F) primer

<400> SEQUENCE: 23
gaaggtgatg caacatacgg aaaa                                       24

<210> SEQ ID NO 24
<211> LENGTH: 25
<212> TYPE: DNA
<213> ORGANISM: Artificial Sequence
<220> FEATURE:
<223> OTHER INFORMATION: GFP(R) primer

<400> SEQUENCE: 24
gtttgtctgc cgtgatgtat acgtt                                      25

<210> SEQ ID NO 25
<211> LENGTH: 102
<212> TYPE: DNA
<213> ORGANISM: Artificial Sequence
<220> FEATURE:
<223> OTHER INFORMATION: The part of DNA sequence translocated with
      heterologous gene by normal recombination in Nicotiana tabacum
      cpDNA

<400> SEQUENCE: 25
gaaataagaa agaagagcta tattcgactg caggcatgca agctatccca attcgggatc    60
tgcgccaggg aaaagaatag aagaagcatc tgactacttc at                     102

<210> SEQ ID NO 26
<211> LENGTH: 162
<212> TYPE: DNA
<213> ORGANISM: Artificial Sequence
<220> FEATURE:
<223> OTHER INFORMATION: The part of DNA sequence translocated with
      heterologous gene by second recombination in a 21Kb subgenome

<400> SEQUENCE: 26

-continued

```
gaaataagaa agaagagcta tattcgaact tgaatctttt gttttctaat ttaaataatg        60
taaaaacgga atgtaagtag gcgagggggc ggatgtagcc aagtggatca aggcagtgga       120
ttgtgaatcc accatgcgcg ggttcaattc ccgtcgttcg cc                          162

<210> SEQ ID NO 27
<211> LENGTH: 118
<212> TYPE: DNA
<213> ORGANISM: Artificial Sequence
<220> FEATURE:
<223> OTHER INFORMATION: The part of DNA sequence between trnA and trnI
      in wild type cpDNA

<400> SEQUENCE: 27
ctaccaactg agctatatcc ccccgagcca agtggagcat gcatgaagta gtcagatgct        60
tcttctattc ttttccctgg cgcagctggg ccatcctgga cttgaaccag agacctcg        118

<210> SEQ ID NO 28
<211> LENGTH: 87
<212> TYPE: DNA
<213> ORGANISM: Artificial Sequence
<220> FEATURE:
<223> OTHER INFORMATION: The part of DNA sequence translocated with
      heterologous gene by second recombination in a 139Kb subgenome

<400> SEQUENCE: 28
ccgagccaag tggagcatgc atgaagtagt cagatgcttc tatcatcaag ctttcgaata        60
tagctcttct ttcttatttc aatgata                                           87
```

PLASTID TRANSFORMATION SYSTEM TO PREVENT THE INTRAMOLECULAR RECOMBINATION OF TRANSGENE

CROSS REFERENCE TO RELATED APPLICATIONS

This is the U.S. §371 National Stage of International Application No. PCT/KR2006/004377, filed Oct. 25, 2006, which was published in English under PCT Article 21(2), which in turn claims priority to Korean Application No. 10-2006-0012477, filed Feb. 9, 2006.

FIELD OF THE INVENTION

The present invention relates to a vector capable of preventing a second intramolecular recombination of a heterologous incorporated into the plastid genome. More specifically, the present invention relates to an expression vector comprising a promoter and a terminator isolated from organisms other than tobacco for plastid transformation.

BACKGROUND OF THE INVENTION

Plastids can be classified as follows: chloroplasts for photosynthesis, leucoplasts lacking in pigments, and chromoplasts involved in the coloring of fruits and flowers. A single plant cell may have up to 200 plastids, and a single plastid may have 100 copies of its genome; thus a single cell may have 10,000~50,000 copies of plastid genome. On the other hand, a nucleus of a plant cell carries only 1 or 2 copies of the genome. Thus, one can produce a heterologous protein using plastid transformation of a gene encoding the heterologous protein about 10,000-fold more effectively than a nuclear transformation Most researches on plastid transformation have been conducted in tobacco (*Nicotiana tabacum*). Successful transformations were reported from such organisms as *Arabidopsis*, potato and tomato, but plants other than tobacco are generally known to suffer from poor transformation efficiencies. The reason why the transformation efficiencies are low seems that the transformation of plastids is carried out inadequately and that long terms and complicated operations are required for selection of transformants as a result. It is possible to achieve highly efficient transformation in tobacco since the natures of transformation have been well known through a number of researches thereon.

Under this rationale, a few plastid transformation methods were recently developed to impart new traits to plants by introducing a heterologous gene (Svab, Z., Hajdukiewicz, Maliga, P., *Proc. Natl. Acad. Sci.*, 87, pp 8526~8530, 1990; Staub, J. M. et al, *Nature Biotechnol.*, 18, pp 333~338, 2000). Such transformation procedures consist of broadly two steps: plastid transformation and selection of transformants.

In order to overcome the problems of low transformation efficiency and long term for selection required for producing homoplasmy in plastid transformation and to develop a simple and efficient procedure for plastid transformation, the present inventors had provided a method of plastid transformation with high rate of homologous recombination and transformation which comprises constructing a vector for plastid transformation comprising a heterologous gene and a selection marker gene, performing plastid transformation by introducing the vector into a plant in which a heterologous recombinase incorporated in a nucleus is designed to translocate into plastids and selecting a transformant according to expression level of the selection marker gene (KR 2002-00218A).

The production of recombinant proteins has been mostly carried out in the microbial and animal cell systems However, researches focused on the production of a recombinant protein using plant and plant cell culture system have been actively in progress. *Agrobacterium*-mediated transformation is mainly used for introducing heterologous genes into plant cells. Unlike microbial systems, plant expression systems do not suffer from the lack of post-translational modification, which can raise value of recombinant proteins produced in plant system. In addition, plant systems have the advantages of less complicated culture condition and use of inexpensive media-compositions compared to animal systems, and less infection from animal viruses and toxins (Doran, P. M. *Current Opinion in Biotechnology*, 11, pp 199~204, 2000). Currently a number of researches have been actively in progress to produce the recombinant protein using the plant cell culture system, and the following model proteins are noteworthy: □-glucuronidase (Kutara, H., Takemura, T., Furusaki, S., Kado, C. I., *J. Ferment. Bioeng.*, 86, pp 317~323, 1998), antibodies (LaCount, W., An, G., Lee, J. M., *Biotechnology Letters*, 19, pp 93~96, 1997), interleukins (Magnuson, N. et al., *Protein Expre. Purif.*, 13, pp 45~52, 1998), ricin (Sehnki, P. C., Ferl, R. J., *Protein Expr. Purif.*, 15, pp 188~195, 1999), and □1-antitrypsin (Terashima, M. et al, *Appl. Microbiol. Biotechnol.*, 52, pp 516~523, 1999).

Tobacco suspension cells or hairy roots are mainly used as host for plant expression systems due to facileness of transformation, relative ease of fluorescence detection and rapid growth rate thereof (Wongsamuth, R., Doran. P. M., *Biotechnol. Bioeng.*, 54(5): 401~415, 1997). In addition, other plants may be used as hosts depending on the choice of a promoter for expressing the recombinant protein. For example, a rice cell culture system can be used, which uses a promoter that senses the depletion in sucrose levels (Terashima, M. et al., *Appl. Microbiol. Biotechnol.*, 52, pp 516~523, 1999).

The promoter/terminator pairs used in the prior arts for chloroplast transformation of tobacco are the promoters and terminators isolated from the same plant species. Such combinations, however, promote another homologous recombination between the terminator and the corresponding sequence in the original chloroplast genome of tobacco in addition to the first homologous recombination, producing plants with anomalies in the chloroplast genome (Staub, J. M., Maliga, P., *Proc. Natl. Acad. Sci.*, 91, 7468~7472, 1994; Svab, Z., Maliga, P., *Proc. Natl. Acad. Sci.*, 90, 913~917, 1993). The present inventors have confirmed that when plastid transformation vectors carrying Prrn/psbAT, a typical promoter/terminator pair were used, 100% of the transformants underwent a second recombination and that 50% of them had anomalous plastid whose genomes consist mostly of small subgenomes arising from the second recombination. In such cases, it was found that stable maintenance and expression of the incorporated heterologous genes were not guaranteed.

DETAILED DESCRIPTION OF THE INVENTION

The principal object of the present invention is to provide a recombinant expression vector for plastid transformation capable of preventing a second homologous recombination. Another object of the present invention is to provide a method for producing transgenic plants using the recombinant expression vector and the transgenic plants produced as such.

In order to achieve the objects mentioned above, the present invention provides a recombinant expression vector for plastid transformation which sequentially comprises an exogenous promoter having low homology to the plastid genome sequences in the target plant, a ribosome-binding sequence (rbs) sequence, and an exogenous terminator having low homology to the plastid genomic DNA of the target plant. Furthermore, the present invention provides a method for producing transgenic plants using said vector. The present invention also provides such transgenic plants as produced from said method.

In the following, the present invention is described in detail.

Upon transformation, conventional chloroplast transformation vectors carrying a promoter/terminator pair from tobacco yield plastid genomes of various sizes. These are produced from a single cross between the psbA terminator originally present in said vector and the psbA terminator present in a heterologous gene (FIG. 1a). Furthermore, a double cross between trnI/psbA terminator sequences existing in the transformation vector, and their counterparts in the plastid genome may create plastid genomes with various sizes as well (FIG. 1b). The present inventors have confirmed such phenomena with polymerase chain reaction (PCR), DNA sequencing and Southern blot analyses (See FIG. 2 to FIG. 7).

Recognizing these problems, the present inventors constructed an expression vector for plastid transformations using the clp promoter from rice (*Oryza sativa*) and the rrnB1/B2 terminator from *Escherichia coli* instead of the rrn promoter and psbA terminator from tobacco (See FIG. 8). The present inventors then constructed a GFP expression vector by inserting a gene encoding green fluorescent protein (GFP), an exogenous protein into said vector and transformed tobacco cells with the newly constructed GFP expression vector. The transformants were then analyzed by PCR using various combinations of primers and probed by Southern blotting for the presence of the heterologous gene. This confirmed that unlike those produced by conventional transformation vectors, the transformants produced by the plastid transformation vector of the present invention do not suffer from a second homologous recombination (See FIG. 9 and FIG. 10). To check whether the incorporated gfp gene is expressed normally, the present inventors monitored GFP activity by fluorescence microscopy. The results showed a normal expression of gfp in the chloroplasts of transformed tobacco cells (FIG. 11) as in the case of using conventional promoters. In addition, the present inventors confirmed that the expression of the exogenous gfp is accompanied by a normal transcription by a Northern blot of the transformants (See FIG. 12).

These results demonstrate the usefulness of the inventive recombinant expression vector for plastid transformation in terms of its capability for preventing second recombinations which is caused by the using of conventional expression vectors. Thus, the vector of this invention can be used in the transformation of plants with a heterologous insuring normal expression thereof.

The recombinant expression vector for plastid transformation sequentially comprises an exogenous promoter with low homology to the plastid genome sequences in the target plant, an rbs sequence, and an exogenous terminator with low homology to the plastid genome. This vector blocks second homologous recombinations inside plastids so as to secure a normal expression of the transgene with which the target plant is transformed.

The exogenous promoter of the inventive recombinant expression vector may be chosen from any exogenous promoter sequence having low homology to the plastid genome of the target plant. By a "promoter" is meant a continuous DNA fragment consisting of more than or equal to 100 nucleotides. Such exogenous promoter sequences include, but are not limited to, sequences preferably having less than 90% homology to the plastid genome; more preferably, less than 80%; still more preferably, 70%; and most preferably less than 50%. The present inventors chose the clp promoter derived from rice. This clp promoter is not limited to, but preferably has the sequence as shown in SEQ. ID NO: 1. Any prokaryotic promoter sequence having low homology to the chloroplast promoter of the target plant may be used for the inventive vector. However, when using rice clp, a rice is excluded from the target plant.

The exogenous terminator of the inventive vector may be chosen from any exogenous terminator sequence having low homology to the plastid genome of the target plant. By a "terminator" is meant a continuous DNA fragment consisting of more than or equal to 100 nucleotides. Such exogenous terminator sequences include, but are not limited to, sequences desirably having less than 90% homology to the plastid genome; more desirably, less than 80%; still more desirably, 70%; and most desirably less than 50%. In addition, such terminator sequence is not limited to, but preferably is derived from prokaryotic terminator sequences, and more preferably derived from the rrnB1/B2 terminator (SEQ. ID NO: 2) of *E. coli* expression vector pHCE19. Any terminator sequence with low homology to the chloroplast promoter of the target plant may be used for the inventive vector.

Selection marker genes may be included in the vector of the present invention. The selection marker genes may include, but not limited to, aadA and gfp. Any gene whose sequence is known to those skilled in the art and which would not interfere with the expression of the heterologous gene is acceptable as the selection marker.

The target plant for the vector of this invention may preferably include, but is not limited to, tobacco, mung beans, kidney beans, peas, potatoes, cassayas, sweet potatoes, soybeans, rape, sunflowers, cotton, tomatoes, eggplants, carrots, red peppers, Chinese cabbages, daikon radishes, watermelons, cucumbers, melons, crown daisies, spinach, cabbages, strawberries, chrysanthemums, roses, carnations, petunias and *Arabidopsis*. In fact, the vector of the present invention may be used against any plant known to those skilled in the art.

The present invention also provides a method for producing transgenic plants using said expression vector. This method comprises the following steps:

1) inserting a heterologous gene into the recombinant expression vector for plastid transformation of the present invention;

2) transforming plant leaf cells with the vector of step 1) in which the heterologous gene is inserted;

3) inducing shoot formation on a selective medium from transformed leaf cells, wherein said shoot is resistant to selection agent(s) of the selective medium;

4) reinducing the induced shoots of step 3) by shoot regeneration;

5) screening transformants by extracting DNA from the reinduced shoots of step 4) and confirming whether the heterologous gene is inserted into plastids; and 6) culturing the transformants screened in step 5).

In the above production method, the presence of the heterologous gene insert in step 5) can be confirmed by, but not limited to such assays as PCR, northern blotting and Southern blotting. Alternative assay methods known to those skilled in the art can be used as well. For PCR analysis, computer programs known to those skilled in the art may be used for designing the primers. In the case of northern or Southern blotting, the probe may be designed by taking advantage of the sequence for the heterologous gene insert or the selective marker gene present in the vector of this invention.

Furthermore, the present invention provides transgenic plants produced by the method described above. The heterologous gene which is to be integrated into the transgenic plant can be chosen from any DNA sequence encoding an exogenous protein of interest to those skilled in the art. For instance, the heterologous genes may include, but are not limited to the following: medicinal proteins with high added-value such as human serum albumin, antibacterial peptides, human interferons ☐. and ☐; vaccines including those against cholera, tetanus, anthrax and animal vaccines; and antibodies.

Meanwhile, the target plant of this invention may preferably include, but is not limited to, tobacco, mung beans, kidney beans, peas, potatoes, cassavas, sweet potatoes, soybeans, rape, sunflowers, cotton, tomatoes, eggplants, carrots, red peppers, Chinese cabbages, daikon radishes, watermelons, cucumbers, melons, crown daisies, spinach, cabbages, strawberries, chrysanthemums, roses, carnations, petunias and *Arabidopsis*.

SUMMARY OF THE INVENTION

The inventive recombinant expression vector for plastid transformation carries the clp promoter derived from rice and rrnB1/B2 terminator from *E. coli* instead of conventional promoter/terminator pairs (rrn promoter/psbA terminator). Such a vector construct supports mass production of exogenous proteins upon plastid transformation as effectively as conventional promoter/terminator constructs, while at the same time, is capable of preventing a second homologous recombination inside plastids.

BRIEF DESCRIPTION OF THE DRAWINGS

FIG. 1 is a schematic diagram depicting a second homologous recombination event when the plastid transformation vector employs the rrn promoter and the psbA terminator derived from tobacco.

FIG. 2 shows the result of a second homologous recombination. A 21 kb subgenome is formed as the heterologous gene moves to a new location.

FIG. 3 is a gel electrophoretogram confirming the second recombination event by PCR. A 21 kb subgenome is formed as the heterologous gene moves to a new location.

FIG. 4 is a DNA sequencing result confirming the second recombination event. A 21 kb subgenome is formed as the heterologous gene moves to a new location. The nucleic acid sequence between psbAT and trnA of the *N. tabacum* chloroplast DNA (SEQ ID NO: 25) is shown (shaded region). The nucleic acid sequence between psbAT and trnH of the rearranged and excised recombinant cpDNA (SEQ ID NO: 26) is also shown.

FIG. 5 is a Southern blot confirming the second recombination event. A 21 kb subgenome is formed as the heterologous gene moves to a new location.

FIG. 6 shows the results from PCR, DNA sequencing and Southern blotting that confirm the occurrence of a second recombination event. A 139 kb subgenome is formed as the heterologous gene moves to a new location. The nucleic acid sequence between trnA and trnI of the wild type cpDNA (SEQ ID NO: 27) is shown (lower sequence). The nucleic acid sequence between trnA and psbA of the 139 kb subgenome (SEQ ID NO: 28) is also shown (upper sequence).

FIG. 7 shows the results from PCR and Southern blotting that confirm the occurrence of a second recombination event. A small 2.8 kb subgenome is newly formed as the heterologous gene moves to a new location.

FIG. 8 is a schematic diagram of the recombinant expression vector for plastid transformation comprising the clp promoter from rice and the rrnB1/B2 terminator from *E. coli*. (a) The trnI-trnA locus in the plastid genome of tobacco into which the heterologous gene is inserted;

(b) A conventional plastid transformation vector comprising the rrn promoter and psbA terminator from tobacco;

(c) The pTIA vector. This vector contains the trnI-trnA locus and provides the backbone for the plastid transformation vector of this invention;

(d) The pRclPADGHT vector. This vector sequentially comprises the rice clp promoter, aadA gene, gfp gene and rrnB1/B2 terminator; and (e) The inventive plastid transformation vector comprising the rice clp promoter, aadA gene, gfp gene and rrnB1/B2 terminator.

FIG. 9 is a Southern blot diagram of tobacco transformants produced by the plastid transformation vector of the present invention.

(a) aadA probe; (b) trnA probe.

FIG. 10 is a PCR gel electrophoretogram of tobacco transformants produced by the plastid transformation vector of the present invention.

(a) I/A primers used;

(b) I/H primers used; and (c) RR23/MK primers used.

FIG. 11 is a fluorescence microscopy photograph of tobacco transformants produced by the inventive plastid transformation vector carrying a gene encoding green fluorescent protein (GFP), an exogenous protein. The expression of GFP in chloroplasts is monitored by its fluorescence.

FIG. 12 shows the results from a northern blot of tobacco transformants produced by the inventive plastid transformation vector carrying gfp, a heterologous gene.

EXAMPLES

The invention is further described in detail by reference to the following experimental examples. These examples are provided for purposes of illustration only, and are not intended to be limited unless otherwise specified.

Example 1

Confirming the Occurrence of a Second Recombination in Plant Transformants Produced with Conventional Chloroplast Transformation Vectors The present inventors constructed CtVG (FIG. 8*b*), a typical chloroplast transformation vector with a GFP insert in the same way as the pTIG vector (Jeong, S. W., Jeong, W. J., Woo, J. W., Choi, D. W., Park, Y. I., Liu, J. R., *Plant Cell Rep.*, 22:741~751, 2004) by modifying the chloroplast transformation vector CtV2 (Guda, G., Lee, S. B., Daniell, H., *Plant Cell Rep.*, 19:257~262, 2000). Chloroplast transformation was carried out with CtVG, and the occurrence of a second recombination in the transformants was investigated as follows.

10~100 ng of genomic DNA isolated from the plastid transformants was used as the template for polymerase chain reaction (PCR). PCRs were performed using exTaq polymerase (Takara, Japan) or AccuPower® PCR premix (Bioneer, Korea) under the conditions of a 5 minutes pre-denaturation at 94° C. followed by 30 cycles of 1 min denaturation at 94° C., 1 minute primer annealing at 55° C. and 1~5 minutes extension at 72° C., and followed by a final chain extension for 10 minutes at 72° C.

All DNA used for Southern blotting was prepared by DNeasy plant minikit (Qiagen, Germany). 4 □g of prepared DNA was digested with BamHI, BglII or EcoRI, respectively, and electrophoresed on a 1% agarose gel, and the DNA was blotted to a Zeta-Probe GT blotting membrane (Bio-Rad, USA). The probes were prepared as follows. The aadA probe was synthesized from the PCR with primers aad5 (SEQ. ID NO: 16) and aad3 (SEQ. ID NO: 17) using the aadA gene in the vector as a template and the corresponding DNA fragment was purified and labeled with [$\alpha$-$^{32}$P]dCTP. The trnA probe was synthesized from the PCR with primers trnAF1 (SEQ. ID NO: 19) and trnAR1 (SEQ. ID NO: 20) using the trnA gene in the vector as a template and the corresponding DNA fragment was purified and labeled with [$\alpha$-$^{32}$P]dCTP. The trnI probe was synthesized from the PCR with primers trnIF3 (SEQ. ID NO: 14) and trnIR4 (SEQ. ID NO: 18) using the trnI gene in the vector as a template and the corresponding DNA fragment was purified and labeled with [$\alpha$-$^{32}$P]dCTP. Pre-hybridization and hybridization were carried out overnight at 65° C. in 0.25M sodium phosphate buffer (pH 7.2) with 7% SDS (w/v). After hybridization, the membrane was washed for 30 minutes with 20 mM sodium phosphate buffer (pH 7.2) containing 5% SDS (w/v) and exposed for 3 hours.

FIG. 1 illustrates how a second recombination generates new plastid genomes of sizes of 21 kb and 139 kb, respectively, in the plastids of transformants produced by conventional transformation vectors carrying promoter/terminator pairs of tobacco origin. First, the diagram demonstrates the single crossover between the psbA loci. Once the foreign gene is introduced into the chloroplast genome, the psbA terminators in the genome and the vector recombine to yield new genomes with different sizes. Since such second recombination events may as well take place between the genomic rrn promoter and its equivalent in the vector, when all possible crossovers are considered, new genomes sizing 154 kb, 139 kb, 21 kb, 18 kb and 2.8 kb can be created. Such second recombination events in which the integrated heterologous gene translocates were confirmed by the detection of DNA fragments sizes of 21 kb, 139 kb and 2.8 using PCR, sequencing and Southern blotting assays (See FIGS. 2 to 7).

In FIG. 3, only those lanes from transformants undergone second recombinations show PCR bands whereas wild type (WT) lanes do not. In the PCR experiment, the following primer pairs were used in anticipation of the resulting genomic sequences: primers I (SEQ. ID NO: 5) and H (SEQ. ID NO: 6); primers RR16 (SEQ. ID NO: 8) and H (SEQ. ID NO: 6); and primers RR16 and RP2 (SEQ. ID NO: 7).

Of the two PCR bands shown in FIG. 4, DNA sequencing proved that the one produced from primers PAF1 (psbA, SEQ. ID NO: 10) and A (trnA, SEQ. ID NO: 9) resulted from a normal recombination, whereas the other produced from primers PAF1 and H (SEQ. ID NO: 6) resulted from a second recombination in which the heterologous gene translocated to a new locus within the plastid genome.

After the plastid transformation, DNA was extracted from the transformants and digested with BamHI or BglII. The digested DNA was subject to Southern blotting with an aadA probe. As observed in FIG. 5, the major bands of 9.3 kb and 6.5 kb result from a normal transformation event, whereas the faint bands of 4.9 kb and 8.9 kb can be traced to the abnormal 21 kb genome (FIG. 2).

Anticipation of expected recombination results (FIG. 6a) and confirmation by DNA sequencing demonstrated that the PCR band produced by primers A (SEQ. ID NO: 9) and PAF1 (NO 10) resulted from the translocation of the introduced heterologous gene within the plastid genome by a second recombination event. The band shown in FIG. 6b results from primers A (SEQ. ID NO: 9) and pAR1 (SEQ. ID NO: 11), and that shown in FIG. 6c results from RR23 (SEQ. ID NO: 12) and MK (SEQ. ID NO: 13), which demonstrates the existence of a 139 kb genome with PCR. FIG. 6d also demonstrates the existence of the 139 kb fragment by Southern blotting. A digested DNA with BamHI/BglII yields a 0.5 kb trnI-trnA band for the wild type genome, whereas it yields a 2.2 kb normal band as well as an anomalous 1.9 kb band for transformed plastid genomes. The presence of the anomalous band again proves a second recombination event responsible for the 139 kb genomic fragment (FIG. 6).

FIG. 7a is a schematic diagram of the 2.8 kb circular DNA generated by a second recombination and its existence is proved in the PCR band (FIG. 7b) produced from primers trnIF3 (SEQ. ID NO: 14) and rrn16R1 (SEQ. ID NO: 15). The generation of this 2.8 kb DNA is corroborated by the Southern blot shown in FIG. 7c. In contrast to the wild type sample, a 2.8 kb band is observed when digested with EcoRI and a small band at 1~2 kb is observed when undigested (FIG. 7).

Example 2

Constructing a Plastid Transformation Vector Comprising the Clp Promoter from Rice (*Oryza sativa*) and the rrnB1/B2 Terminator from *E. coli*

Using rice genomic DNA as a template, a DNA fragment comprising the clp promoter was amplified by PCR with rclpP5 primer (SEQ. ID NO: 3) and rclpP3 primer (NO 4) and subcloned into the pCR2.1-TOPO vector (Invitrogen, USA). The exTaq DNA polymerase (Takara, Japan) was employed for the PCR under the conditions of a 5-minute pre-denaturation at 94° C. followed by 30 cycles of a 1-minute denaturation at 94° C., a 1-minute primer annealing at 55° C. and a 1-minute extension at 72° C., and followed by a final extension for 10 minutes at 72° C. The amount of rice genomic DNA template was 10~100 ng. The sequence of rice clp promoter (SEQ. ID NO: 1) was confirmed by nucleotide sequencing. The rrnB1/B2 terminator (SEQ. ID NO: 2) was prepared by a digestion of pHCE19, a commercial *E. coli* expression vector (Takara, Japan), with PstI/HincII to obtain an 800 bp fragment.

Meanwhile, using 10~100 ng of tobacco genomic DNA as the template, a 1.95 kb trnI-trnA border DNA sequence was amplified by PCR with the I-L1 primer (SEQ. ID NO: 21) and I-R2 primer (NO 22). The exTaq DNA polymerase (Takara, Japan) was employed for the PCR under the conditions of 94° C. for 5 minutes followed by 30 cycles of 94° C. for 1 minute, 55° C. for 1 minute and 72° C. for 2 minutes, and followed by a final 10 minutes extension at 72° C. The amplified DNA fragment was digested with XbaI/KpnI, made blunt-ended by the Klenow enzyme, and cloned into pUC18 at a PvuII site to construct the pTIA backbone vector (FIG. 8c). An aadA-gfp DNA fragment isolated from this pTIG vector was subcloned into the pBlueScript KSII vector (Stratagene, USA) with SalI/PstI. The resulting product was digested with BamHI/SmaI and made blunt-ended by the Klenow enzyme. The rrnB1/B2 DNA fragment mentioned above was ligated to the digested vector. This was followed by the subcloning of the rclp promoter at the XhoI/SalI site to yield the pRclPADGHT vector (FIG. 8d). An rclp-aadA-gfp-rrnB1/B2 DNA fragment digested with XhoI and EcoRI, made blunt-ended with the Klenow enzyme and subcloned into a PvuII site of the pTIA backbone vector to yield the pRclPADGHT vector (FIG. 8e), a plastid transformation vector containing rice clp promoter and *E. coli* rrnB1/B2 terminator.

Example 3

Producing Transgenic Plants by the Plastid Transformation Vector pRclPADGHT Plastid transformation was carried out as follows using the vector pRclPADGHT. As a control group, the transformation was carried out with CtVG, a conventional transformation vector having the rrn promoter and psbA terminator.

Wild type tobacco (*Nicotiana tabacum* var. *Samsun*) seeds were allowed to germinate in vitro for 8 weeks and then the leaves were taken and placed on an MS medium (Murashige, T., Skoog, F., *Physiol. Plant*, 15:473~49, 1962) with 1 mg/L benzyl aminopurine (BAP) and 0.1 mg/L □-napthalene acetic acid (NAA) for plastid transformation. Using $CaCl_2$ and spermidine, a plastid transformation vector carrying gfp as a heterologous gene was coated onto gold particles having an average diameter of 0.6 m. The particles were then delivered to the leaves at an acceleration power of 1,100 psi with a target distance of 9 cm in a vacuum of 28 inches (Hg) by the PDH-1000/He gene delivery system (BioRad, USA).

The treated leaves were cultured for 2 days at 25° C. in a light condition of 2,000 lux. The leaves were then cut into fragments of 2~5 mm sizes and cultured for 6~7 weeks in an MS medium with 1 mg/L BAP, 0.1 mg/L NAA and 500 mg/L spectinomycin to induce resistant shoots. These spectinomycin-resistant shoots were cut into 3 mm×3 mm pieces and were allowed to regenerate in the same medium for re-induction of resistant shoots. Such regeneration of resistant shoots was repeated to reach a full homoplasmy of the inserted gene.

Example 4

The Southern Blot of Transgenic Plants Produced by the Plastid Transformation In order to confirm the presence of the heterologous gene and its homoplasmy in the resulted transgenic tobacco and the presence of anomalous genomes generated from second recombinations, a Southern blot analysis with the aadA, trnA or trnI probe was performed. All DNA for the Southern blot analysis was prepared with the DNeasy plant minikit (Qiagen, Germany). All procedures for the Southern blot analysis, such as DNA digestion of the transformants, PCR, and probe preparation with restriction digestion were carried out in the same manner as described in Example 1.

The DNA from transformants produced by the vector containing the rice clp promoter and rrnB1/B2 terminator was digested with BglII and probed with aadA (FIG. 9). No band was observed for the wild type sample, but a main band of 6.5 kb and a faint minor one of 8.9 kb were observed in lane C for the control group transformants, which were produced with the vector carrying the rrn and psbA elements. This result confirms the generation of the 21 kb genome fragment by a second recombination. On the other hand, transformants produced with the vector of the present invention which contains the rice clp and rrnB1/B2 elements yielded only a single 7.2 kb band (FIG. 9a) and no other band in all 3 lanes (lanes 1~3).

The Southern blot results with the trnA probe (FIG. 9b) exhibited a 4.47 kb band for the wild type and one main band of 6.5 kb and a faint minor band of 1.9 kb for the control group (rrn/psbA, lane C), confirming the existence of the 139 kb genome fragment by a second recombination. In contrast, transformants produced by the vector of the present invention (clp/rrnB1/B2) yielded only a single 7.2 kb band (FIG. 9a) in all 3 lanes (lanes 1~3) but no other band. Except for the wild type sample, the 4.47 kb band was hardly observable. These results corroborate the conclusion that all the plastid genomes of the regenerated transformants contain the exogenous DNA to reach homoplasmy (FIG. 9b).

The present inventors were able to conclude that the inventive plastid transformation vector is capable of preventing the generation of anomalous genome fragments such as the 21 kb and 139 kb fragments from second recombination events.

Example 5

PCR Analysis of Tobacco Transformants for the Occurrence of a Second Recombination In order to check whether a second recombination takes place in transformants produced by the inventive plastid transformation vector with the rice clp and rrnB1/B2 elements, the present inventors carried out a PCR analysis. The same conditions as used in Example 1 were employed for the PCR. PCR with primers I (SEQ. ID NO: 5) and A (SEQ. ID NO: 9) shows that all transformants have the heterologous gene insert normally integrated into their plastids (FIG. 10a). In addition, PCR with primers I (SEQ. ID NO: 5) and H (SEQ. ID NO: 6) detected bands only in the control samples and none in the 10 transformants produced by the inventive vector with the rice clp and rrnB1/B2 elements (FIG. 10b). Identical patterns were obtained with primers RR23 (SEQ. ID NO: 12) and MK (SEQ. ID NO: 13), wherein only the control samples had PCR bands.

These results confirm the absence of anomalous genome fragments produced by second recombination events in tobacco plastid transformants in the case of transformation by the vector with rice clp promoter and *E. coli* rrnB1/B2 terminator elements.

Example 6

Monitoring GFP Expression in Tobacco Plastid Transformants

In order to monitor the expression of GFP in transgenic tobacco produced by the inventive transformation vector carrying a GFP insert, the present inventors isolated leaf cells from tobacco transformants and carried out fluorescence microscopy. FIG. 11 indicates the plants transformed by the inventive vector construct (clp/rrnB1/B2) shows a normal expression of GFP in the chloroplasts as that by a conventional construct.

Example 7

Northern Blotting of Tobacco Plastid Transformants

The present inventors confirmed the expression of the heterologous gene in tobacco transformants produced by the inventive transformation vector (rice clp promoter/rrnB1/B2 terminator) by northern blot analysis using RNA isolated from their leaves. All RNA for the northern blot analysis was isolated with the RNeasy plant minikit (Qiagen, Germany). 5 g of the isolated RNA was electrophoresed in a 1% agarose gel and was blotted to a Zeta-Probe GT blotting membrane (Bio-Rad, USA). The membrane was probed with a gfp probe. Primers GFP(F) (SEQ. ID NO: 23) and GFP(R) (SEQ. ID NO: 24) were used for the PCR with the same conditions as used in Example 1. Pre-hybridization and hybridization were carried out overnight at 65° C. in 0.25 M sodium phosphate buffer (pH 7.2) with 7% SDS (w/v). This was followed by washing the membrane with 20 mM sodium phosphate buffer (pH 7.2) with 5% SDS (w/v) at 65° C. for 30 minutes. The washed membrane was exposed on X-ray film for an hour.

FIG. 12 indicates the plants transformed by the inventive vector construct (clp/rrnB1/B2) shows a normal high level expression of the GFP mRNA in the chloroplasts of the transformants.

INDUSTRIAL APPLICABILITY

The inventive recombinant expression vector for plastid transformation is capable of mass-producing exogenous proteins on a level par with conventional vectors containing promoter/terminator pairs isolated from tobacco. At the same time, the vector of the present invention is capable of preventing second recombination events within plastids. Therefore, the vector of the present invention is greatly useful in producing transgenic plants since it can insure a secure incorporation of heterologous genes and support normal transformation and heterologous gene expression.

LIST OF SEQUENCES

The Sequence Listing is submitted as an ASCII text file in the form of the file named Sequence_Listing.txt, which was created on Jun. 29, 2010, and is 7737 bytes, which is incorporated by reference herein.

SEQ. ID NO: 1 is the sequence for rice clp (*Oryza sativa*) promoter.
SEQ. ID NO: 2 is the sequence for *E. coli* rrnB1/B2 terminator.
SEQ. ID NO: 3 is the sequence for the primer rclpP5.
SEQ. ID NO: 4 is the sequence for the primer rclpP3.
SEQ. ID NO: 5 is the sequence for the primer I.
SEQ. ID NO: 6 is the sequence for the primer H.
SEQ. ID NO: 7 is the sequence for the primer RP2.
SEQ. ID NO: 8 is the sequence for the primer RP16.
SEQ. ID NO: 9 is the sequence for the primer A.
SEQ ID NO: 10 is the sequence for the primer PAF1.
SEQ. ID NO: 11 is the sequence for the primer pAR1.
SEQ ID NO: 12 is the sequence for the primer RR23.
SEQ. ID NO: 13 is the sequence for the primer MK.
SEQ. ID NO: 14 is the sequence for the primer trnIF3.
SEQ ID NO: 15 is the sequence for the primer rrn16R1.
SEQ. ID NO: 16 is the sequence for the primer aad5.
SEQ. ID NO: 17 is the sequence for the primer aad3.
SEQ. ID NO: 18 is the sequence for the primer trnIR4.
SEQ. ID NO: 19 is the sequence for the primer trnAF1.
SEQ. ID NO: 20 is the sequence for the primer trnAR1.
SEQ. ID NO: 21 is the sequence for the primer I-L1.
SEQ. ID NO: 22 is the sequence for the primer I-R2.
SEQ. ID NO: 23 is the sequence for the primer GFP(F)
SEQ. ID NO: 24 is the sequence for the primer GFP(R).
SEQ ID NO: 25 is the part of the DNA sequence translocated with the heterologous gene by normal recombination in *Nicotiana tabacum* cpDNA.
SEQ ID NO: 26: is the part of the DNA sequence translocated with the heterologous gene by a second recombination in a 21 kb subgenome.
SEQ ID NO: 27 is the part of the DNA sequence between trnA and trnI in wild type cpDNA.
SEQ ID NO: 28 is the part of the DNA sequence translocated with the heterologous gene by a second recombination in a 139 kb subgenome.

What is claimed is:

1. A recombinant expression vector for plastid transformation comprising an expression construct sequentially comprising a promoter, a ribosome binding site sequence and a terminator, wherein the promoter and terminator are exogenous to a target plant to be transformed, wherein the promoter has less than 50% homology to the plastid genome of the target plant, and wherein the terminator is a rrnB1/B2 terminator, wherein the expression construct is flanked by DNA sequences homologous to sequences in the plastid genome of the target plant.

2. The recombinant expression vector according to claim 1, wherein the promoter is a clp promoter derived from rice (Oryza sativa), and wherein the target plant does not include rice.

3. The recombinant expression vector according to claim 1, wherein the promoter is either of prokaryotic origin or derived from chloroplast promoters of plants other than the target plant.

4. The recombinant expression vector according to claim 1, wherein the rrnB1/B2 terminator comprises the nucleic acid sequence of SEQ ID NO: 2.

5. The recombinant expression vector according to claim 1, wherein the rrnB1/B2 terminator is derived from E. coli.

6. The recombinant expression vector according to claim 1, additionally comprising a selection marker gene.

7. The recombinant expression vector according to claim 6, wherein the selection marker gene is either aadA or gfp.

8. A method for producing transgenic plants by plastid transformation comprising the steps of:
   1) inserting a heterologous gene sequence into the recombinant expression vector of claim 1;
   2) transforming the leaves of a target plant with the recombinant expression vector of step 1), comprising said heterologous gene sequence;
   3) inducing resistant shoots from transformed leaves of step 2) using a selective medium;
   4) re-inducing shoot formation by allowing the shoots of step 3) to regenerate themselves;
   5) screening for transformants by extracting DNA and/or RNA from the reinduced shoots of step 4) and confirming the presence of said heterologous gene sequence; and
   6) culturing the transformants screened in step 5).

9. The method for producing transgenic plants according to claim 8, wherein polymerase chain reaction, northern blot analysis, or Southern blot analysis is used for the screening in step 5).

10. A transgenic plant produced by the method of claim 8.

11. The transgenic plant according to claim 10, wherein the target plant is selected from the group consisting of: tobacco, mung bean, kidney bean, pea, potato, cassava, sweet potato, soybean, rape, sunflower, cotton, tomato, eggplant, carrot, red pepper, Chinese cabbage, daikon radish, watermelon, cucumber, melon, crown daisy, spinach, cabbage, strawberry, chrysanthemum, rose, carnation, petunia and Arabidopsis.

* * * * *

UNITED STATES PATENT AND TRADEMARK OFFICE
CERTIFICATE OF CORRECTION

PATENT NO. : 7,888,562 B2  
APPLICATION NO. : 12/159595  
DATED : February 15, 2011  
INVENTOR(S) : Liu et al.

Page 1 of 1

It is certified that error appears in the above-identified patent and that said Letters Patent is hereby corrected as shown below:

In the Specification:

Column 4, line 33, "cassayas," should read --cassavas,--.

Column 5, line 14, "cassayas," should read --cassavas,--.

Column 9, line 21, "0.6 m" should read --0.6 µm--.

Column 10, lines 61-62, "5 g" should read --5 µg--.

In the Claims:

Claim 4, col. 21, line 56, "rmB1/B2" should read --rrnB1/B2--.

Claim 11, col. 22, line 58, "cassaya," should read --cassava,--.

Signed and Sealed this  
Ninth Day of April, 2013

Teresa Stanek Rea  
*Acting Director of the United States Patent and Trademark Office*